(12) United States Patent
Ding et al.

(10) Patent No.: US 6,673,385 B1
(45) Date of Patent: Jan. 6, 2004

(54) METHODS FOR POLYMERIC COATINGS STENTS

(75) Inventors: Ni Ding, San Jose, CA (US); Deborra Sanders Millare, San Jose, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/893,957

(22) Filed: Jun. 28, 2001

Related U.S. Application Data

(63) Continuation-in-part of application No. 09/583,683, filed on May 3, 2000.

(51) Int. Cl.[7] .......................... A61L 27/00; A61L 27/28; A61L 27/54; B05D 1/02
(52) U.S. Cl. ...................... 427/2.28; 427/2.1; 427/2.24; 427/2.25; 427/2.3; 427/508; 427/487; 427/421
(58) Field of Search ................................ 427/2.1, 2.24, 427/2.25, 2.28, 2.3, 508, 487, 421

(56) References Cited

U.S. PATENT DOCUMENTS

| | | | |
|---|---|---|---|
| 5,118,779 A | 6/1992 | Szycher ....................... 528/75 |
| 5,693,034 A | 12/1997 | Buscemi et al. ............. 604/265 |
| 5,782,908 A * | 7/1998 | Cahalan et al. ............. 623/1.13 |
| 5,804,318 A * | 9/1998 | Pinchuk et al. ............. 428/421 |
| 5,863,650 A * | 1/1999 | Healy et al. ................ 427/2.11 |
| 5,980,972 A | 11/1999 | Ding .......................... 427/2.24 |
| 6,005,020 A | 12/1999 | Loomis ....................... 523/105 |
| 6,013,855 A * | 1/2000 | McPherson et al. ...... 623/23.76 |
| 6,083,524 A * | 7/2000 | Sawhney et al. ............ 424/426 |
| 6,100,346 A * | 8/2000 | Jamiolkowski et al. ..... 525/419 |
| 6,107,416 A * | 8/2000 | Patnaik et al. .............. 525/453 |
| 6,221,425 B1 | 4/2001 | Michal et al. .............. 427/2.25 |
| 6,242,041 B1 * | 6/2001 | Katoot et al. .............. 427/2.24 |

\* cited by examiner

*Primary Examiner*—Shrive P. Beck
*Assistant Examiner*—Jennifer Kolb Michener
(74) *Attorney, Agent, or Firm*—Squire, Sanders & Dempsey, L.L.P.

(57) ABSTRACT

This invention provides a method of forming a polymeric coating for a stent. The method can comprise applying a prepolymer or a combination of prepolymers to the stent and initiating polymerization to form a polymeric coating for the stent. The coating material can optionally contain a biologically active agent or combination of agents.

18 Claims, No Drawings

METHODS FOR POLYMERIC COATINGS STENTS

CROSS-REFERENCE

This application is a continuation-in-part of U.S. patent application Ser. No. 09/583,683 filed on May 31, 2000.

BACKGROUND OF THE INVENTION

1. Field of the Invention

This invention relates to a method for coating stents.

2. Description of the Background

Stents act as scaffoldings, functioning to physically hold open and, if desired, to expand the wall of a passageway. Typically stents are capable of being compressed, so that they can be inserted through small vessels via catheters, and then expanded to a larger diameter once they are at the desired location. Mechanical intervention via stents has reduced the rate of restenosis; restenosis, however, is still a significant clinical problem. Accordingly, stents have been modified not only to perform as a mechanical scaffolding, but also to provide biological therapy.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A common method of medicating a stent is by depositing a polymeric coating, impregnated with the therapeutic substance, on the surface of the stent. A polymer dissolved in a solvent is applied to the stent. A therapeutic substance can be dissolved or dispersed in the composition. The solvent is allowed to evaporate to form the coating. The application of the composition can be performed by spraying the composition on the stent or immersing the stent in the composition. A problem associated with the application of a polymeric solution includes coating defect such as "cob webs" and "pool webs." "Cob webs" are defined as the gathering of the polymeric coating between the stent struts once the solvent has been removed. "Pool webs" are clumps or pools of polymer on the struts. "Cob webs" and "pool webs" are caused by high viscosities associated with the composition and the surface tension of the polymer and the solvent. Moreover, increasing the quantity of the polymer applied to the stent, so as to increase the drug loading of the stent, further promulgates the development of such defects. Accordingly, a method is needed to reduce or significantly eliminate coating defects on a stent.

SUMMARY

A method of forming a polymeric coating on a stent is provided. In one embodiment, the method can comprise the acts of applying a monomer or a combination of monomers to the stent and initiating polymerization of the monomer or combination of monomers to form a polymeric coating on the stent. The act of applying can be conducted by spraying the monomer or monomers at the stent. The polymerization can be initiated by radical chain reaction or step-function reaction. The polymerization can be initiated by the inclusion of a photochemical and exposure of the stent to a light energy source or by the inclusion of a thermal initiator and exposure of the stent to a thermal energy source. In one embodiment the monomer or monomers can be in a liquid phase or can be added to a solvent or a combination of solvents to effect dissolution of the monomer(s). The method can also include applying an active agent to the stent. The active agent can be applied separately or added to the monomer or at least one of the monomers of the combination.

In accordance with another embodiment, a method of forming a polymeric coating on a stent is provided comprising spraying a radially expandable stent with a coating fluid, the fluid comprising a prepolymer and causing the prepolymer to react to form a polymeric coating on the stent. The fluid can optionally include an additive for increasing the viscosity of the fluid. The fluid can also include an active agent for the treatment of restenosis, or alternatively, the active agent can be applied in a separate application step.

In accordance with another embodiment a method of forming a polymeric coating for a stent is provided comprising applying an oligomer or a combination of oligomers to the stent; and initiating polymerization of the oligomer or combination of oligomers to form a polymeric coating for the stent.

In accordance with another embodiment a method of forming a polymeric coating for a stent is provided comprising applying a macromer or a combination of macromers to the stent; and initiating polymerization of the macromer or combination of macromer to form a polymeric coating for the stent.

DETAILED DESCRIPTION OF THE EMBODIMENTS

Monomers or monomeric chemical compounds are generally defined as the building material from which a polymer is formed such as by step-function (condensation), radical chain (addition) polymerization, or ionic polymerization processes. Monomeric chemical compounds are to be distinguished from oligomers and macromonomers. Oligomers are defined as polymer intermediates containing relatively few structural units. Polymers having a reactive group at one end and intended for further reaction are called macromonomers, or in conventional abbreviation, macromers. Polymer or polymeric compounds are inclusive of homopolymers, copolymers, terpolymers etc., including random, alternating, block and graft variations thereof. The term "prepolymer" as used herein after is intended to include one or a combination of different monomers, oligomers, and macromers that are capable of forming a polymer. Should any of the prepolymers be in a solid phase at operating temperatures, e.g., ambient temperature and pressure, the prepolymer can be dissolved in a solvent system for application to a stent.

In accordance with one embodiment, a monomer or a combination of monomers can be applied to a stent for coating the stent. The monomer can be any chemical which can be polymerized to form a suitable, biocompatible coating on the stent. Examples of the monomer can include, but are not limited to, vinyl, acrylate and allyl compounds such as any monomer with one or more vinyl, acrylate or allyl double bonds. Specific examples of some suitable monomers include 2-hydroxyethyl methacrylate (HEMA); glycol methacrylate; methyl methacrylate; ethyl methacrylate; butyl methacrylate; sulfanato ethyl methacrylate; ethylene vinyl acetate; ethyl acrylate; acrylamide; urethane-acrylate; acrylamide-ethyl methacrylate; di-vinyl benzene; triethylene glycol divinyl ether; tri-methylol propane tri-acrylate; pentaerythritol tetra-acrylate; Bisphenol A ethoxylate diacrylate; allyl ether, di-allyl maleate; vinyledene fluoride; and tri-allyl isocyanurate. Additionally, unsaturated monomers such as cell adhesion promoting, non-fouling, or anti-restenotic monomers can be used to form the coating or as additives to be used in conjunction with other prepolymers. Examples include vitamin E methacrylate, phenoxyethylmethacrylate, dimethyl amino ethyl methacrylate, vinyl pyrrolidone, polyethylene glycol methacrylate, sulfonated Dextran, methacryloxy phosphoryl choline, methacrylate acid, acrloyl, and methacryloyl. The combination of different monomers can form polymers with properties suitable for drug impregnation and stent coating.

In accordance with another embodiment, an oligomer or combination of oligomers can be used to coat the stent. A representative example includes urethane-acrylate (e.g., Cognis 6892, formerly Henckel 12-892).

In accordance with another embodiment, a macromer or a combination of macromers can be used to coat the stent. Representative examples include, but are not limited to polyethylene glycol diacrylates and polycaprolactone diacrylate.

Subsequent to the application of the prepolymers, polymerization is induced to form a polymeric coating on the stent by, for example, photoinitiated polymerization reaction as is well understood by one of ordinary skill in the art. Briefly, light of short enough wavelength (e.g., 320–800 nm) or, in other words, high enough energy per quantum can initiate polymerization directly. The light energy can be provided by any appropriate source to generate the desired radiation, such as mercury-arc lamps, fluorescent lamps with special phosphors, long wave ultra violet lamps, He-Ne laser or an argon ion laser. A photochemical initiator such as benzophenone, 2,2-dimethoxy-2-phenylacetophenone, 1-hydroxycyclohexyl phenyl ketone, benzoin ethyl ether, and phenyl azide are typically used. Means other than light can also be used for polymerization. For example, thermal initiators can be used which form free radicals at moderate temperatures. Free radical polymerization initiators are compounds with bonds that easily undergo thermal hemolytic scission, e.g., hydroperoxides (RO—OH); peroxides (RO—OR'), peresters (RCOO—OR'), azo compounds (RN=NR') and persulfate compounds ($O_4S$—$SO_4$). These initiators thermally decompose at the illustrated bond. Representative examples can include benzoyl peroxide, with or without triethanolamine, potassium persulfate, with or without tetramethylethylenediamine, bis(2,4-dichlorobenzoyl) peroxide; dicumyl peroxide; 2,5-bis(tert-butyl peroxy)-2,5-dimethyl hexane; ammonium persulfate, and 2,2'-azobisisobutyronitrile and ammonium persulfate with sodium bisulfite. Each initiator requires a different temperature to induce decomposition.

High-energy radiation from a wide variety of sources, including electrons, gamma rays, x-rays, and slow neutrons, is also effective in producing free radicals that can initiate polymerization of the monomers. With the use of photoinitiated polymerization reaction, however, the rate of generation of free radicals can be controlled with high precision since the generation of radicals can be made to vary instantaneously by controlling the intensity of the initiating light.

In accordance with another embodiment of the present invention, an active agent can be combined with the prepolymer or with a solvent system in which such the prepolymer is dissolved. Alternatively, the active agent can be co-applied or pre-applied by any suitable liquid carrier. The active agent should be applied as a true solution or a saturated solution. If the active agent is not completely soluble, operations including mixing, stirring, and/or agitation can be employed to effect homogeneity of the residues. The active agent may be added in fine particles. The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycino from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substanices. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Representative examples of solvent systems for effectuating the dissolution should the prepolymer be in solid phase include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

In accordance with another embodiment, a fluid can be used to adjust or increase the "wetting" of the prepolymer or the solvent system or to increase the solubility of the active agent in the prepolymer or the solvent system. Accordingly, higher active agent concentrations can be formulated. "Wetting" is defined by capillary permeation. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of the wetting fluid include, but are not limited to, tetrahydrofuran (THF), dimethylformamide (DMF), 1-butanol, n-butyl acetate, dimethylacetamide (DMAC), and mixtures and combinations thereof.

To form a coating on the stent, the prepolymer or combination of prepolymers with or without a solvent system, can be applied to both the inner and outer (the tissue contacting) surface of the stent. Application can be by any method, such as by spraying the composition onto the stent or immersing the stent in the composition. If more than one monomer, oligomer or macromer is employed, each prepolymer can be combined and applied as a single solution, can be applied to the stent concomitantly in the spray application, or each compound can be applied in a sequence of application steps. Because prepolymers, specially monomers, have a relatively low viscosity, some of which can be less than 2.5 centipoise at room temperature, the use of prepolymers for making a polymeric coating would allow for a more fluent application of the coating which can minimize coating defects such as "cob webs" or "pool webs." Should the viscosity of the monomer be too low so as not to allow a suitable retention of the monomer on a stent, a viscosifying agent may be required. Examples of the agent can include polymers of the same prepolymer(s) to be applied such a polyvinyl pyrrolidone and poly-n-butylmethacrylate. Other examples can include glucose, caster oil, cotton seed oil, and glycerol. The molar ratio of the viscosifying agent could be less than 60%, more narrowly less than 50% of the prepolymer. An alternative method of increasing the retention of the prepolymer on the surface of the device would be to decrease the temperature during and/or subsequent to the application of the prepolymer to below room temperature. Providing a cooler environment leads to an increase in the viscosity.

In addition to creating a less viscose delivery platform, monomeric compounds may allow for a better dissolution of the active agent with the monomer or the monomer-solvent combination. Many of the active agents are hydrophilic and can only dissolve with highly polar counterparts. Polymers have a tendency of being less polar than their monomeric constituents. Accordingly, a better dissolution is achieved by the use of a monomeric delivery system.

The prepolymers can be used to form a basecoat or a primer layer, a reservoir layer, and/or a topcoat or rate limiting barrier layer. As for deposition of the outermost coating layer, a second functional or anchoring monomer can be included in the formulation which would allow for the surface modification of the outermost layer. For example, the addition of a small amount of cinnamaldehyde or isocyanato ethyl methacrylate could introduce aldehyde or isocyanate functional groups on the surface of the layer. Accordingly, biocompatible components such as heparin and polyethylene glycol can be covalently bonded to the surface of the coating.

The type of stent used in the practice of the present invention is not of critical importance. Stents are broadly defined to include radially expandable stents such as balloon-expandable stents or self-expandable stents and stent-grafts. The stents can be vascular or non-vascular type stents. One of ordinary skill in the art understands that the coating application of the present invention can also be used with a variety of other medical devices, such as grafts, heart valves, endocardial leads, and other implantable devices. The stent can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the process.

EXAMPLES

The following examples are given by way of illustration:

Example 1

N-butyl methacrylate is mixed with azobisisobutyronitrile at the weight ratio of 1:100 (AIBN/BMA). The solution can be sprayed on the surface of the stent. The stent can be baked at a temperature of 50° C. or above necessary to initiate polymerization. To increase the weight or thickness of the coating, small amounts of PBMA (e.g., <1%) can be added to the system to increase the viscosity, or the coating and baking cycle can be repeated until a desired weight or thickness is reached.

Example 2

25% methylmethacrylate, 9% n-butyl methacrylate, 8% PEG methacrylate (6k MW), in 55% DMAC and 3% photo-initiator are prepared (concentrations in mole %). The composition can be sprayed on the stent. UV illumination will be applied for 10 minutes. A non-solvent such as hexane can be added to precipitate the final polymer.

Example 3

9% of n-butylmethacrylate, 8% of PEG methacrylate (6k MW), and 20% sulfanato ethyl methacrylate in 40% DMAC, 20% ethanol and 3% photo-initiator can be prepared (concentrations in mole %). Solution is sprayed and UV illumination is applied to the stent for 10 minutes. A non-solvent such as Hexane will be added to precipitate the final polymer.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of forming a polymeric coating for a stent, comprising:
   (a) applying a mixture of a monomer or a combination of monomers and an initiator of polymerization to the stent; and (b) initiating polymerization of the monomer or combination of monomers by subjecting the stent to thermal treatment or by exposing the stent to UV radiation, to form a polymeric coating for the stent, wherein:
  (i) the polymer forming the coating is selected from a group consisting of poly(glycol methacrylate), poly(methyl methacrylate), poly(ethyl methacrylate), poly(butyl methacrylate), poly(sulfanato ethyl methacrylate), poly(ethylene-co-vinyl acetate), poly(ethyl acrylate), poly(urethane-acrylate), poly(acrylamide-co-ethyl methacrylate), poly(divinyl benzene), poly(triethylene glycol-co-divinyl ether), poly(tri-methylol propane triacrylate), poly(pentaerythritol tetraacrylate), poly(Bisphenol A ethoxylate diacrylate), poly(allyl ether), poly(diallyl maleate), poly(vinylidene fluoride), poly(triallyl isocyanurate), and blends thereof, and
  (ii) the initiator is selected from a group consisting of benzophenone, 2,2-dimethoxy-2-phenylacetophenone, 1-hydroxycyclohexyl phenyl ketone, benzoin ethyl ether, phenyl azide, 2,2'-azobisisobutyronitrile, potassium persulfate, ammonium persulfate, and a blend of ammonium persulfate with sodium bisulfite.

2. The method of claim 1, wherein the act of applying comprises spraying the monomer or monomers at the stent.

3. The method of claim 1, wherein the polymerization is initiated by radical chain reaction.

4. The method of claim 1, wherein the polymerization is initiated by step-function reaction.

5. The method of claim 1, wherein the monomer or monomers are added to a solvent or a combination of solvents prior to application to the stent.

6. The method of claim 1, wherein the monomer or at least one of the combination of monomers is in a fluid phase at room temperature.

7. The method of claim 1, additionally including applying an active agent to the stent.

8. The method of claim 1, additionally including mixing an active agent with the monomer or at least one of the monomers if a combination of monomers is used such that the active agent is contained in the polymeric coating for sustained release after the stent has been implanted in a subject.

9. The method of claim 1, wherein the monomer comprises acrylate, vinyl or allyl compounds.

10. The method of claim 9, wherein the acrylate compound is selected from a group consisting of, glycol methacrylate, methyl methacrylate, ethyl methacrylate, butyl methacrylate, sulfanato ethyl methacrylate, ethyl acrylate, and mixtures thereof.

11. A method of forming a polymeric coating on a stent, comprising:
  (a) spraying a radially expandable stent with a coating fluid, the fluid comprising a prepolymer and an therapeutic agent mixed with the prepolymer; and
  (b) causing the prepolymer to react to form a polymeric coating on the stent, wherein the active agent is contained in the polymeric coating, and wherein the polymer forming the coating is selected from a group consisting of poly(glycol methacrylate), poly(methyl methacrylate), poly(ethyl methacrylate), poly(butyl methacrylate), poly(sulfanato ethyl methacrylate), poly(ethylene-co-vinyl acetate), poly(ethyl acrylate), poly(urethane-acrylate), poly(acrylamide-co-ethyl methacrylate), poly(divinyl benzene), poly(triethylene glycol-co-divinyl ether), poly(tri-methylol propane triacrylate), poly(pentaerythritol tetraacrylate), poly(Bisphenol A ethoxylate diacrylate), poly(allyl ether), poly(diallyl maleate), poly(vinylidene fluoride), poly(triallyl isocyanurate), and blends thereof.

12. The method of claim 11, wherein the fluid comprises an additive for increasing the viscosity of the fluid.

13. The method of claim 11, wherein the therapeutic agent is for the treatment of restenosis.

14. The method of claim 11, wherein the act of causing the polymer to react is initiated by step-function, radical chain reaction, or ionic polymerization processes.

15. The method of claim 11, additionally comprising applying to the stent a second fluid containing at least one other prepolymer, different than the prepolymer of the fluid, wherein the prepolymers of the fluid and second fluid are capable of reacting to form a polymeric coating.

16. The method of claim 11, additionally comprising applying to the stent a monomer for creating functional groups on the surface of the polymeric coating.

17. A method of forming a polymeric coating for a stent, comprising:
  (a) applying a mixture of an oligomer or a combination of oligomers and an initiator of polymerization to the stent; and
  (b) initiating polymerization of the oligomer or combination of oligomers by subjecting the stent to thermal treatment or by exposing the stent to UV radiation, to form a polymeric coating for the stent, wherein:
    (i) the polymer forming the coating is poly(urethane-acrylate); and
    (ii) the initiator is selected from a group consisting of benzophenone, 2,2-dimethoxy-2-phenylacetophenone, 1-hydroxycyclohexyl phenyl ketone, benzoin ethyl ether, phenyl azide, 2,2'-azobisisobutyronitrile, potassium persulfate, ammonium persulfate, and a blend of ammonium persulfate with sodium bisulfite.

18. A method of forming a polymeric coating for a stent, comprising:
  (a) applying a macromer or a combination of macromers to the stent; and
  (b) initiating polymerization of the macromer or combination of macromers to form a polymeric coating for the stent, wherein the polymer forming the coating is selected from a group consisting of poly(ethylene glycol diacrylate) and poly(caprolactone diacrylate).

* * * * *